United States Patent

Vandenbossche et al.

[11] Patent Number: 5,123,402
[45] Date of Patent: Jun. 23, 1992

[54] MEDICAL INSTRUMENT SHIELD

[76] Inventors: Ben Vandenbossche, 245 W. Santa Inez; R. Cameron Emmott, 229 Bridge, both of Hillsborough, Calif. 94010

[21] Appl. No.: 398,831

[22] Filed: Aug. 25, 1989

[51] Int. Cl.$^5$ .............................................. A61B 1/00
[52] U.S. Cl. ............................................ 128/7; 128/857
[58] Field of Search ............. 604/117, 174, 177, 178, 604/268, 355–357; 128/7, DIG. 26, 857, 863, 887.4; 239/103–105

[56] References Cited

U.S. PATENT DOCUMENTS

| | | | |
|---|---|---|---|
| 1,555,003 | 9/1925 | Greenberg et al. | 128/7 |
| 1,662,227 | 3/1928 | Allyn | 128/7 |
| 1,679,950 | 8/1928 | Stern | 606/46 |
| 4,080,970 | 3/1978 | Miller | 604/174 |
| 4,516,968 | 5/1985 | Marshall et al. | 604/174 |
| 4,593,681 | 6/1986 | Soni | 128/4 |
| 4,700,890 | 10/1987 | Hasegawa | 239/103 |
| 4,834,068 | 5/1989 | Gottesman | 128/4 |
| 4,848,322 | 7/1989 | Dash et al. | 128/4 |
| 4,958,623 | 9/1990 | Rocco | 128/7 |

Primary Examiner—C. Fred Rosenbaum
Assistant Examiner—C. Maglione
Attorney, Agent, or Firm—Joseph L. Strabala

[57] ABSTRACT

A see-through shield for a urological or similar medical instrument for treating bladder and prostate problems, includes a cylindrical collar adapted to fit a boss on the instrument, a clear planner shield element, a hollow cone-shaped connecting member having its apex connected to one end of the collar and its skirt connected to the shield element forming a semi-flexible joint between the collar and the shield element, a radial slit from and through the collar, the cone-shaped member and into a portion of the shield element to allow a portion of the instrument larger than the collar diameter to pass through the shield when attaching it to an instrument and a securing means to clamp the collar on the boss of an instrument.

7 Claims, 1 Drawing Sheet

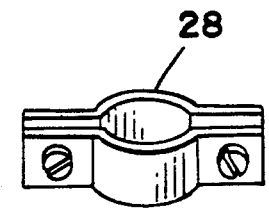
FIG_4
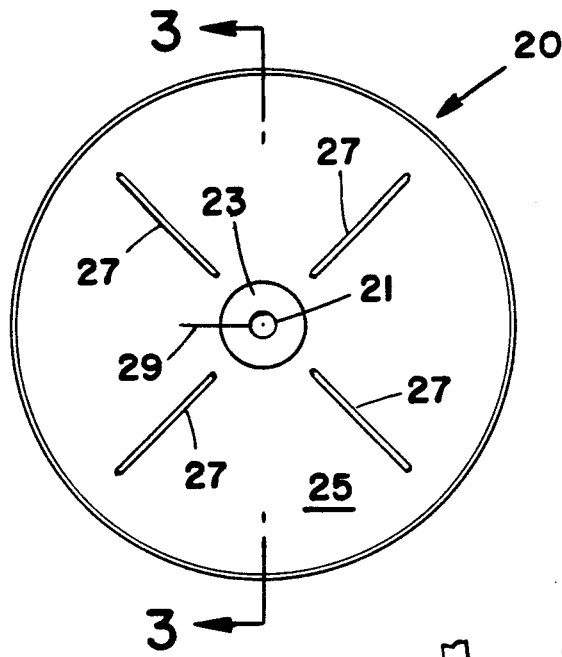
FIG_2
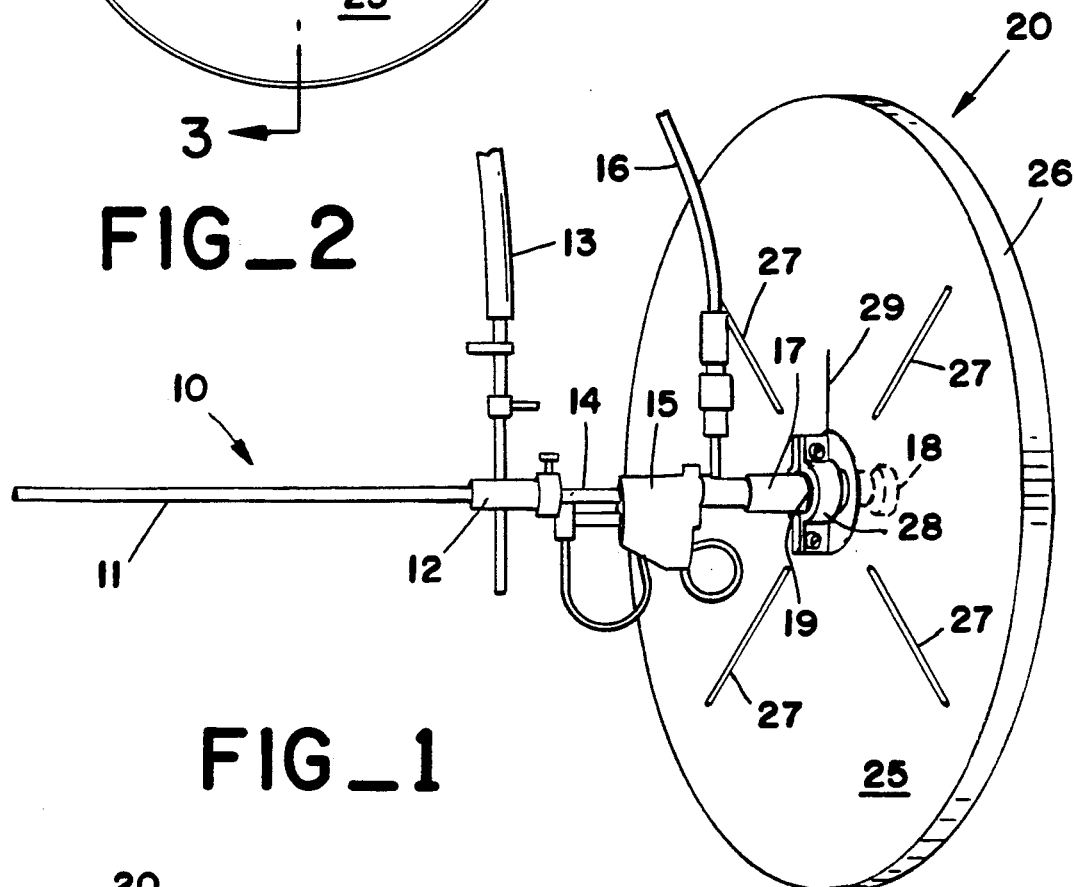
FIG_1
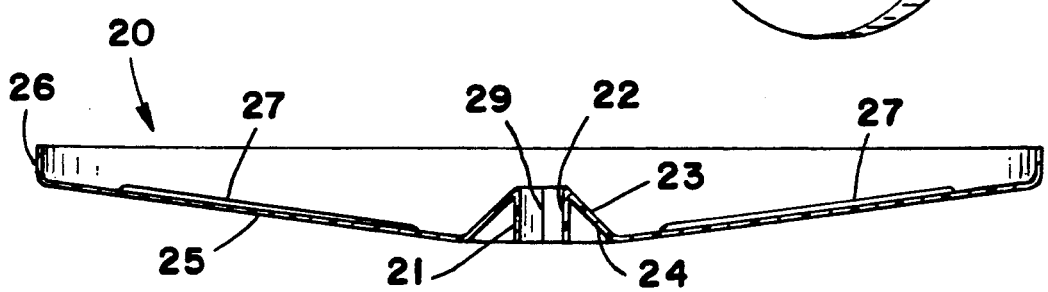
FIG_3

MEDICAL INSTRUMENT SHIELD

BACKGROUND OF DISCLOSURE

Developments in miniaturization and optics have provided new instruments and techniques to treat various medical problems. Examples are the "Cystoscope" and the "Resectoscope" used to treat bladder and prostate maladies.

When using such instruments, which are less intrusive than other types of surgery, procedures require that the bladder be irrigated with fluids to enable diagnosis and surgical procedures using the associated optics in the instruments.

These irrigating fluids become contaminated with blood and tissue during the surgical procedures and the contaminated fluids must be drained and replaced before the physician can continue. In these instruments the eye piece is retracted so the contaminated fluids can drain from the bladder into a receptacle. Egress of such fluids from the bladder during such procedures may splash the physician with these fluids since he must still manipulate the instrument while carrying out this procedure. Also, when the eye piece is re-inserted into the instrument, some of the fluid is sprayed from the joint during this procedure. As the blood, the tissue, the prostate and the bladder all may host infectious diseases, such as AIDS, there is a need to isolate the physician from such fluids while allowing him to continue to observe the patient and operate the instrument. Thus, a useful shield must also satisfy this function.

Such a shield must also be deflectable since the physician must perform the procedures in close proximity to the natural body openings of the bladder. This usually requires the physician accomplish the procedures from a location between the patient's legs with the patient in a dorsal lithotomy position which is also known as the "birthing position". Therefore the shield must be connected to the instrument with a semi-flexible joint to allow deflection thereof when the situation demands as the instrument must be moved up and down, as well as from right to left during the procedures whereby it may contact the patient or the operating table. If the shield did not deflect in such circumstances it would interfere with the physician's procedures.

The current shield meets the criteria outlined above. In addition, it provides an economical protective shield which can be discarded after each use because of its low cost.

Of course, the instant invention has other advantages, as will be obvious from the description of it and in the accompanying drawings.

SUMMARY OF THE INVENTION

A clear shield element for use with medical instruments for treating urological disorders includes a cylindrical collar means adapted to fit a boss on the instrument, a clear generally flat shield element with a central aperture oriented normal to the longitudial axis of the collar means, a hollow conical member having its apex connected to one end of the cylindrical collar means and its flared skirt connected to the aperture of the shield element operable to form a semi-flexible joint between the collar means and the shield element, a radial slit from and through the collar means, the conical member and partially into the shield element operable to allow parts of the instrument larger than the diameter of the collar means to pass through the shield, and a securing means operable to clamp the collar on the boss of the instrument.

The planar shield element may include a flange, normal to its surface plane located at its periphery to increase its structural rigidity. Also radial ribs can be incorporated into the shield element for this same purpose.

BRIEF DESCRIPTION OF THE DRAWINGS

FIG. 1 is a perspective of the novel shield of this invention assembled with the medical instrument on which it is used;

FIG. 2 is a front elevation of the novel shield element;

FIG. 3 is a section along lines 3—3 of FIG. 2; and,

FIG. 4 is a perspective of a clamp used to secure the shield to an instrument.

DESCRIPTION OF A PREFERRED EMBODIMENT

Referring to FIG. 1, the instrument 10 is shown assembled with the novel shield 20. As can be seen in this drawing, the instrument includes catheter 11 which is inserted into the patient's bladder through the uretha. A manifold is joined to the catheter and connected to a fluid line 13. Connecting tubes 14 join the manifold to a second manifold 15 with a second fluid line 16 connected to it. An eye piece assembly 17 with an eye piece 18 is connected to the second manifold, as shown, with one of the connecting tubes being part of the eye piece. On the eye piece assembly is a cylindrical boss 19 to which the shield 20 is secured.

When the instrument is inserted irrigating fluid is provided through the fluid lines. After diagnosis, surgical procedures cause the irrigating fluid to become contaminated with blood and tissue and it must be drained from the bladder before the physician can continue. To accomplish this procedure the physician retracts a portion of the eye piece (one of tubes 14) from the first manifold 12 of the instrument. This will allow the contaminated irrigating fluid from the bladder to drain into a receptacle below the first manifold adjacent to the face of the physician.

Once the contaminated irrigating fluid is drained from the bladder, the eye piece is returned to its initial position during which procedure some of the contaminated fluid is sprayed from the joint. Thereafter, fresh irrigating fluid is pumped into the bladder so the physician can resume the procedure.

The construction of the novel shield 20 is more detailed in FIG. 3. As can be seen in this cross-section, it is preferable of a one-piece construction, formed from single clear plastic sheet, such as by vacuum forming. It is about 30 mils in thickness, made from commercial plastic products such as PETG from Sheffield, Inc.

In the preferred embodiment, the shield 20 is circular, about 12 inches in diameter, and includes a cylindrical collar 21 which is adapted to fit onto the boss 19 of the instrument 10. The collar is connected to the apex 22 of a conical member 23 which has its flared skirt 24 joined about a central aperture in the planar shield element 25 which shield is oriented normal to the longitudinal axis of the collar 21. This shield element is slightly dished, as shown in FIG. 3, to enhance its rigidity and it may include radially disposed ribs 27 formed by depressions in its surface to also increase its rigidity.

The flat shield element 25 has its surface plane oriented generally normal to the axis of the collar 21 and that of the conical member 23. In the preferred embodiment this shield element may include a flange 26 about its peripheral edge oriented generally normal to its planar surface to stabilize its edge and protect the patient from injury.

With the above described configuration, once the collar 21 is secured to boss 19 of the instrument with a clamp 28, the conical member 23 acts as a semi-rigid joint allowing the shield element to articulate about the collar when the instrument is being manipulated by the physician and the shield contacts some object.

In actual tests in operating rooms, the shield's performance was exceptional, allowing a full range of the use of the instrument with the added protection the shield provided.

As can be seen in FIG. 1, the eye piece 18 is of a much larger diameter than the bore of the collar 21. Thus, the shield normally could not be assembled with the instrument without disassembly of the eye piece assembly 17 which is undesirable. To accommodate its assembly, without instrument disassembly, a radial slot 29 is cut from and through the collar 21, the conical member 23 and partially into the shield element 25, as best shown in FIG. 2. As a result, these parts will separate under pressure allowing the eye piece 18 to be simply pushed through the deflecting parts or the shield 20 which thereafter return to their initial position. Thereafter the collar 21 is clamped on boss 19 with clamp 28. It has been found that the clamp can be replaced with vinyl tape which may be used to cinch the collar on boss 19. Also, if desired such tape can be used to seal the radial slit 29, to provide further protection for the physician.

In another embodiment the inside surface of the collar 21 can be coated with adhesive (not shown) to further stabilized the shield 20 on the boss 19.

Having described my invention I claim:

1. A medical instrument shield for use with devices employing rigid catheters comprising:
   a hollow cylindrical collar adapted to fit on a boss of a rigid medical instrument;
   a clear generally planar shield element of plastic oriented normal to the longitudinal axis of said hollow collar means, said element having a central aperture;
   a hollow conical member having its apex sealingly connected to one end of said cylindrical collar means and its flared skirt sealingly connected to said shield element about its aperture operable to form a semi-flexible joint between said collar means and said shield element;
   a radial slit extending from and through said collar means, through said conical member and partially into said shield element operable to allow said parts to deflect when assembled over parts of the instrument larger than the diameter of said collar means and,
   securing means operable to secure said collar means on a boss of an instrument to be used with said shield.

2. The shield as defined in claim 1 wherein its several parts are formed from a integral sheet of clear plastic material having a thickness of approximately 30 millimeters.

3. The shield as defined in claim 2 wherein the shield element is circular in configuration.

4. The shield as defined in claim 3 wherein the shield element includes a flange oriented generally normal to its surface and disposed at its circular periphery.

5. The shield defined in claim 3 wherein the shield element is slightly dished to increase its rigidity.

6. The shield defined in claim 3 wherein the shield element includes a plurality of radially disposed ribs in its central portion to increase its rigidity.

7. In a rigid medical instrument used to treat urological disorders having a catheter and an eye piece, a disposable shield element comprising:
   a hollow cylindrical collar means sized to fit on a boss associated with a rigid instrument;
   a generally clear planar shield element of plastic oriented normal to the axis of said collar, said element having a central aperture;
   a hollow conical member having its apex sealingly connected to one end of said collar means and its flared skirt sealingly connected to said shield element about its central aperture operable to form a semi-flexible joint between said collar means and said shield element;
   a radial slit extending from and through said collar means, said conical member and partially into said shield element operable to allow said parts to deflect over portions of said instrument when said shield is assembled and disassembled therewith, and
   securing means for clamping said collar on said instrument.

* * * * *